United States Patent
Yoshida et al.

(10) Patent No.: US 10,138,469 B2
(45) Date of Patent: Nov. 27, 2018

(54) SYNTHETIC PEPTIDE AND USE THEREOF

(71) Applicants: Toagosei Co., Ltd., Tokyo (JP); Keio University, Tokyo (JP); National University Corporation Nagoya University, Aichi (JP)

(72) Inventors: Tetsuhiko Yoshida, Ibaraki (JP); Nahoko Baileykobayashi, Ibaraki (JP); Mikio Niwa, Ibaraki (JP); Jun Kudo, Tokyo (JP); Tomohiro Izumiyama, Tokyo (JP); Makoto Sawada, Aichi (JP)

(73) Assignees: Toagosei Co., Ltd., Tokyo (JP); Keio University, Tokyo (JP); National University Corporation Nagoya University, Aichi (JP)

( * ) Notice: Subject to any disclaimer, the term of this patent is extended or adjusted under 35 U.S.C. 154(b) by 7 days.

(21) Appl. No.: 15/321,276

(22) PCT Filed: Jun. 22, 2015

(86) PCT No.: PCT/JP2015/067924
§ 371 (c)(1),
(2) Date: Dec. 22, 2016

(87) PCT Pub. No.: WO2015/199041
PCT Pub. Date: Dec. 30, 2015

(65) Prior Publication Data
US 2017/0233701 A1 Aug. 17, 2017

(30) Foreign Application Priority Data
Jun. 23, 2014 (JP) .................. 2014-128436

(51) Int. Cl.
*C12N 5/074* (2010.01)
*A61K 38/00* (2006.01)
*C07K 7/06* (2006.01)
*C07K 14/00* (2006.01)

(52) U.S. Cl.
CPC ............ *C12N 5/0696* (2013.01); *A61K 38/00* (2013.01); *C07K 7/06* (2013.01); *C07K 14/00* (2013.01); *C12N 2501/40* (2013.01); *C12N 2506/1307* (2013.01)

(58) Field of Classification Search
CPC .......... A61K 38/00; C07K 14/00; C07K 7/06; C12N 2501/40; C12N 2506/1307; C12N 5/0696
See application file for complete search history.

(56) References Cited

U.S. PATENT DOCUMENTS

| | | | |
|---|---|---|---|
| 2009/0068742 A1 | 3/2009 | Yamanaka | |
| 2010/0297758 A1 | 11/2010 | Yoshida et al. | |
| 2015/0011469 A1* | 1/2015 | Tso ................... | A61K 38/1709 514/6.9 |
| 2015/0267174 A1 | 9/2015 | Hayashi et al. | |
| 2016/0346346 A1 | 12/2016 | Baileykobayashi et al. | |

FOREIGN PATENT DOCUMENTS

| | | |
|---|---|---|
| WO | WO2007/069666 | 6/2007 |
| WO | WO2009/093692 | 7/2009 |
| WO | WO2011/158852 | 12/2011 |
| WO | WO2014/057997 | 4/2014 |

OTHER PUBLICATIONS

Fong et al. Cell (2011) 147: 120-131 (Year: 2011).*
Extended Search Report issued in EP 15811420.7—dated Feb. 1, 2018.
Warren, et al. "Highly Efficient Reprogramming to Pluripotency and Directed Differentiation of Human Cells with Synthetic Modified mRNA" Cell Stem Cell 7, 618-630, Nov. 5, 2010.
Salisbury et al., "Centrin-2 is Required for Centriole Duplication in Mammalian Cells", Current Biology, vol. 12, 1287-1291, Aug. 6, 2002.
Garcia et al., UniProtKB-A0A023FK29, Jun. 11, 2014.
Takahashi et al., "Induction of Pluripotent Stem Cells from Mouse Embryonic and Adult Fibroblast Cultures by Defined Factors" Cell 126, 663-676, Aug. 25, 2006.
Kim et al., Generation of Human Induced Pluripotent Stem Cells by Direct Delivery of Reprogramming Proteins, Cell Stem Cell 4, 472-476, Jun. 5, 2009.

* cited by examiner

*Primary Examiner* — Susan M Hanley
(74) *Attorney, Agent, or Firm* — Occhiuti & Rohlicek LLP

(57) ABSTRACT

Provided are a synthetic peptide that induces the reprogramming of a differentiated cell, a reprogramming-inducing pharmaceutical composition that contains this synthetic peptide, and a method for producing an undifferentiated cell from a differentiated cell using this synthetic peptide. The peptide provided by the present invention is a synthetic peptide having a reprogramming-inducing peptide sequence formed of the amino acid sequence given by SEQ ID NO: 1 or a modified amino acid sequence thereof. The method for producing an undifferentiated cell provided by the present invention includes inducing the reprogramming of a target cell by culturing a cell culture which contains the target cell and to which the synthetic peptide has been supplied.

9 Claims, 6 Drawing Sheets
Specification includes a Sequence Listing.

FIG. 7

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Cys Lys Ser Lys Ser Arg Arg Ser Cys
1               5

<210> SEQ ID NO 2
<211> LENGTH: 13
<212> TYPE: PRT
<213> ORGANISM: Homo sapiens

<400> SEQUENCE: 2

Lys Lys Arg Thr Leu Arg Lys Asn Asp Arg Lys Lys Arg
1               5                   10

<210> SEQ ID NO 3
<211> LENGTH: 8
<212> TYPE: PRT
<213> ORGANISM: Avian infectious bronchitis virus

<400> SEQUENCE: 3

Trp Arg Arg Gln Ala Arg Phe Lys
1               5

<210> SEQ ID NO 4
<211> LENGTH: 11
<212> TYPE: PRT
<213> ORGANISM: Human immunodeficiency virus

<400> SEQUENCE: 4

Tyr Gly Arg Lys Lys Arg Arg Gln Arg Arg Arg
1               5                   10
```

```
<210> SEQ ID NO 5
<211> LENGTH: 11
<212> TYPE: PRT
<213> ORGANISM: Artificial sequence
<220> FEATURE:
<223> OTHER INFORMATION: Synthetic peptide

<400> SEQUENCE: 5

Tyr Ala Arg Ala Ala Ala Arg Gln Ala Arg Ala
1               5                   10

<210> SEQ ID NO 6
<211> LENGTH: 16
<212> TYPE: PRT
<213> ORGANISM: Drosophila melanogaster

<400> SEQUENCE: 6

Arg Gln Ile Lys Ile Trp Phe Gln Asn Arg Arg Met Lys Trp Lys Lys
1               5                   10                  15
```

SYNTHETIC PEPTIDE AND USE THEREOF

CROSS REFERENCE TO RELATED APPLICATIONS

This application is a National Stage of International Application No. PCT/JP2015/067924 filed on Jun. 22, 2015, which claims priority to Japanese Application No. 2014-128436 filed on Jun. 23, 2014, the contents of which are hereby incorporated by reference in their entirety.

TECHNICAL FIELD

The present invention relates to a novel synthetic peptide and use thereof. More specifically, the present invention relates to a peptide that can induce the reprogramming of a cell that has undergone differentiation (differentiated cell), a composition having this peptide as an effective component, and the use of the peptide and composition.

This application claims priority based on Japanese Patent Application No. 2014-128436 filed on Jun. 23, 2014, and the contents of this Japanese application are incorporated in their entirety in this Description by reference.

BACKGROUND ART

Pluripotent stem cells are undifferentiated cells that have the capacity to differentiate into the various cell types that form an organism (pluripotency). Pluripotent stem cells also have the capacity to undergo self-renewal (self-renewal capacity) in a state in which pluripotency is maintained (typically an undifferentiated state) and as a consequence can be cultured (maintained) on a long-term basis in a state in which pluripotency is maintained (typically an undifferentiated state). In view of this pluripotency and self-repair capacity (proliferative capacity), there are high expectations for pluripotent stem cells as a cell resource for use in regenerative medicine, for example, cell transplantation therapy. These pluripotent stem cells can be specifically exemplified by induced pluripotent stem cells (also referred to as "iPS cells" hereinafter), embryonic stem cells (also referred to as "ES cells" hereinafter), and muse cells (multi-lineage differentiating stress enduring cell).

In particular, iPS cells are cells that have acquired pluripotency and self-renewability through an artificial reprogramming of differentiated cells (typically somatic cells, for example, dermal fibroblasts). That is, iPS cells can be produced using a patient's own somatic cells (differentiated cells). Due to this, rejection reactions and ethical problems either do not occur with iPS cells or are minor, and as a consequence iPS cells are expected to be cells that have advantages as a cell resource for regenerative medicine and research into their clinical applications has been rapidly advancing.

CITATION LIST

Patent Literature

Patent Literature 1: WO 2007/069666
Patent Literature 2: WO 2009/093692

Non Patent Literature

Non Patent Literature 1: Cell, Volume 126, 2006, pp. 663-676

Non Patent Literature 2: Cell Stem Cell, Volume 4, 2009, pp. 472-476
Non Patent Literature 3: Cell Stem Cell, Volume 7, 2010, pp. 618-630
Non Patent Literature 4: Current Biology, Volume 12, 2002, pp. 1287-1292

SUMMARY OF INVENTION iPS cells are produced by the reprogramming of differentiated cells by the introduction of a plurality of reprogramming factors into differentiated cells (typically somatic cells). A set of several genes (for example, the four genes for Oct 3/4, klf4, c-Myc, and Sox2) is typically used for these reprogramming factors (Patent Literature 1 and Non Patent Literature 1). Problems occur in the art of reprogramming differentiated cells through gene transduction, e.g., the potential for the incorporation of the transduced genes into the genome (potential for gene insertion), the reprogramming efficiency, and the complexity of the process. With the goal of solving these problems (in particular avoiding the potential for gene insertion), efforts have been made to improve the gene transduction method and to establish art for reprogramming differentiated cells through the introduction of gene products (for example, RNA or protein) from the genes used as the aforementioned reprogramming factors (Non Patent Literature 2 and Non Patent Literature 3).

The present invention was created taking as a problem the development of a novel art that could artificially bring about the reprogramming of a differentiated cell. In specific terms, an object of the present invention is to provide a novel artificial peptide that has a relatively short chain and can be artificially synthesized and that induces reprogramming of a target differentiated cell (for example, a somatic cell). Another object is to provide a composition (pharmaceutical composition) that contains this peptide and thus contributes to the goal of inducing the reprogramming of a differentiated cell. Additional objects are to provide a method for producing an undifferentiated cell by reprogramming a differentiated cell using this peptide and to provide the undifferentiated cell produced by this method.

The present inventors carried out intensive investigations with regard to artificially synthesizable, relatively short-chain peptides and surprisingly discovered for the first time that a differentiated cell could be reprogrammed by supplying to the differentiated cell a peptide synthesized so as to contain the amino acid sequence given by SEQ ID NO: 1 and culturing under prescribed culture conditions. The present invention was achieved based on this discovery. The amino acid sequence given in SEQ ID NO: 1 is a sequence that is unrelated to the proteins whose use as reprogramming factors has heretofore been attempted (for example, the gene products of genes (Oct 3/4, klf4, c-Myc, and Sox2, and so forth) that are used a reprogramming factors).

In order to realize the aforementioned objects, the present invention provides an artificially synthesized peptide (also referred to herebelow as the "reprogramming-inducing peptide") that is characterized by having the capacity (also referred to herebelow as the "reprogramming-inducing activity"), when supplied to a differentiated cell (typically when added to the medium on which the cell is being cultured), to induce the reprogramming of this cell.

That is, the herein disclosed synthetic peptide (reprogramming-inducing peptide) is a peptide that is artificially synthesized and that induces reprogramming of at least one type of differentiated cell, the synthetic peptide having a reprogramming-inducing peptide sequence formed of the following amino acid sequence:

(SEQ ID NO: 1)
CKSKSRRSC or a modified amino acid sequence that is obtained by the substitution, deletion, and/or addition of 1, 2, or 3 amino acid residues in the amino acid sequence and that induces reprogramming in at least one type of differentiated cell.

The herein disclosed synthetic peptide (reprogramming-inducing peptide) characteristically has the reprogramming-inducing peptide sequence in its peptide chain. As a consequence of this, the induction of the reprogramming of a target differentiated cell can be accomplished by a simple and convenient method in which the reprogramming-inducing peptide is supplied to the target differentiated cell (typically in the medium in which the cell is cultured) and culturing is carried out.

In addition, the use of the herein disclosed reprogramming-inducing peptide makes it possible to induce the reprogramming of a differentiated cell without using the reprogramming factors (typically genes, DNA) that have been used in conventional methods for producing iPS cells. In other words, because the reprogramming of a target differentiated cell can be induced by the supply of a synthetic peptide, the introduction of foreign genes into the genome that could be caused by gene transduction is not a concern.

Moreover, the herein disclosed synthetic peptide (reprogramming-inducing peptide) has a simple structure (typically a linear peptide chain) and can be easily artificially produced by chemical synthesis (or biosynthesis). The use of the herein disclosed reprogramming-inducing peptide also enables the induction of reprogramming of a target cell without using large amounts of, e.g., expensive humoral factors, as typified by differentiation inhibitory factors (for example, bFGF, LIF, and so forth), and as a consequence enables the low-cost realization of reprogramming of a target differentiated cell. As a result, the herein disclosed synthetic peptide is a preferred component for a composition used for the purpose of inducing reprogramming of differentiated cells. In addition, it can be used in methods for producing undifferentiated cells by the reprogramming of differentiated cells.

In a preferred aspect of the herein disclosed synthetic peptide (reprogramming-inducing peptide), the total number of amino acid residues constituting the peptide chain is characteristically not more than 30.

A peptide having such a short peptide chain has a high structural stability (for example, resistance to protease) and has excellent handling properties and storage properties. Moreover, a peptide having such a short peptide chain is preferred because it is easily chemically synthesized and can be produced (acquired) at relatively inexpensive production costs.

In another aspect, the present invention provides a composition (pharmaceutical composition) for use to induce the reprogramming of at least one type of differentiated cell (this composition is also referred to herebelow as the "reprogramming-inducing agent"), wherein the composition contains a synthetic peptide according to any of the herein disclosed aspects (the reprogramming-inducing peptide) and at least one pharmaceutically acceptable carrier (for example, at least one substrate or liquid medium, e.g., physiological saline or various buffers, that contributes to enhancing the stability of the peptide).

Because it contains the hereabove-described reprogramming-inducing peptide, a composition with this construction can induce the reprogramming of a target differentiated cell when the composition is supplied to the differentiated cell (typically in the medium in which the cell is cultured). Such a composition (reprogramming-inducing agent) can in particular be advantageously used for the purpose of inducing the reprogramming of a differentiated cell (for example, a fibroblast) of human origin or non-human mammal origin.

In another aspect, the present invention is a method for producing an undifferentiated cell by reprogramming at least one type of differentiated cell, wherein the production method includes preparing a cell culture that contains a target cell; supplying to the cell culture the synthetic peptide (reprogramming-inducing peptide) according to any of the herein disclosed aspects; and culturing the cell culture to which the peptide has been supplied and thereby inducing reprogramming of the target cell.

This method for producing an undifferentiated cell can efficiently produce an undifferentiated cell in an in vitro culture system without having to carry out complex processes such as, e.g., gene transduction. In addition, this method for producing an undifferentiated cell can produce an undifferentiated cell by reprogramming a target differentiated cell (and a structure formed of this cell) through a simple and convenient procedure of supplying the synthetic peptide with the simple structure described above (or a composition containing this synthetic peptide) to a cell culture (typically in the medium on which the cell is cultured) and culturing. Since gene transduction is not required by this method for producing an undifferentiated cell, the insertion of a transgene in the genome of the undifferentiated cell is then not a concern. Moreover, this method for producing an undifferentiated cell is a preferred method for producing an undifferentiated cell because it can induce the reprogramming of a differentiated cell in a highly reproducible manner without requiring a complex procedure and/or a special apparatus.

Further, this method for producing an undifferentiated cell can produce an undifferentiated cell from a differentiated cell without using large amounts of, e.g., expensive humoral factors, as typified by differentiation inhibitory factors (for example, bFGF, LIF, and so forth) (typically without using these humoral factors) and can maintain the undifferentiated cell in an undifferentiated state on a long-term basis. Due to this, production of the undifferentiated cell and maintenance of the produced undifferentiated cell can be realized at low cost.

A preferred aspect of the herein disclosed method for producing an undifferentiated cell is characterized in that the target differentiated cell is a human fibroblast. The method of the present invention for producing undifferentiated cells can be advantageously applied to the objective of producing undifferentiated cells from human fibroblasts (for example, fibroblasts of epidermal tissue origin).

Undifferentiated cells produced from cells of human origin have a very high utility in the medical sector (the fields of regenerative medicine, new drug development, basic medicine, and so forth). In addition, fibroblasts are cells that have a high proliferative capacity and are easily cultured (maintained) in in vitro culture systems (monoculture is typically possible) and as a consequence undifferentiated cells can be efficiently produced by using these cells as the target differentiated cell.

In another aspect, the present invention provides an undifferentiated cell that has been produced by any of the herein disclosed methods of producing undifferentiated cells. For this undifferentiated cell, typically an undifferentiated cell is provided that characteristically expresses at least 1 (preferably at least 2, more preferably at least 3, and still more preferably at least 4) endogenous gene selected from the group of Oct3/4, Nanog, Sox2, TRA1-81, SSEA-3, and alkaline phosphatase (also referred to as "ALP" hereinafter).

Because the introduction of foreign genes is not required in this production process, this undifferentiated cell is then a cell for which the tumorigenicity caused by the insertion of foreign genes into the genome is not a concern.

In addition, endogenous Oct3/4, Nanog, Sox2, TRA1-81, SSEA-3, and ALP are genes that are specifically expressed by pluripotent stem cells (for example, ES cells, iPS cells, and so forth), and it is known that the expression of these genes declines (and is typically extinguished) as differentiation advances. Due to this, the expression of these genes (that is, the presence of protein obtained by transcription from these genes and translation) is widely used as an index (marker) showing that a cell is in an undifferentiated state, i.e., is widely used as undifferentiated marker. In addition, the expression of these genes is also used as an index (marker) showing that a cell possesses pluripotency, i.e., as a pluripotency marker. Accordingly, an undifferentiated cell that expresses at least 1 endogenous gene (preferably at least 2, more preferably at least 3, and even more preferably at least 4) selected from the group of Oct3/4, Nanog, Sox2, TRA1-81, SSEA-3, and ALP can be favorably used as a cell resource for regenerative medicine.

BRIEF DESCRIPTION OF DRAWINGS

FIG. 7 contains optical micrographs (images) that show the status of fibroblasts that have been cultured under different cell culture temperature conditions and different conditions of addition of a reprogramming-inducing peptide (sample 1) according to a working example, wherein images are given for observation in each instance on the 1st, 2nd, 3rd, 4th, 5th, and 6th days after the start of culture and, in the images for the temperature conditions of 13° C. and 22° C. observed on the 6th day after the start of culture with the addition of a reprogramming-inducing peptide (sample 1) according to a working example, the region encompassed by the circle at the base of the arrow is shown enlarged at the tip of the arrow.

DESCRIPTION OF EMBODIMENTS

Figure 1:
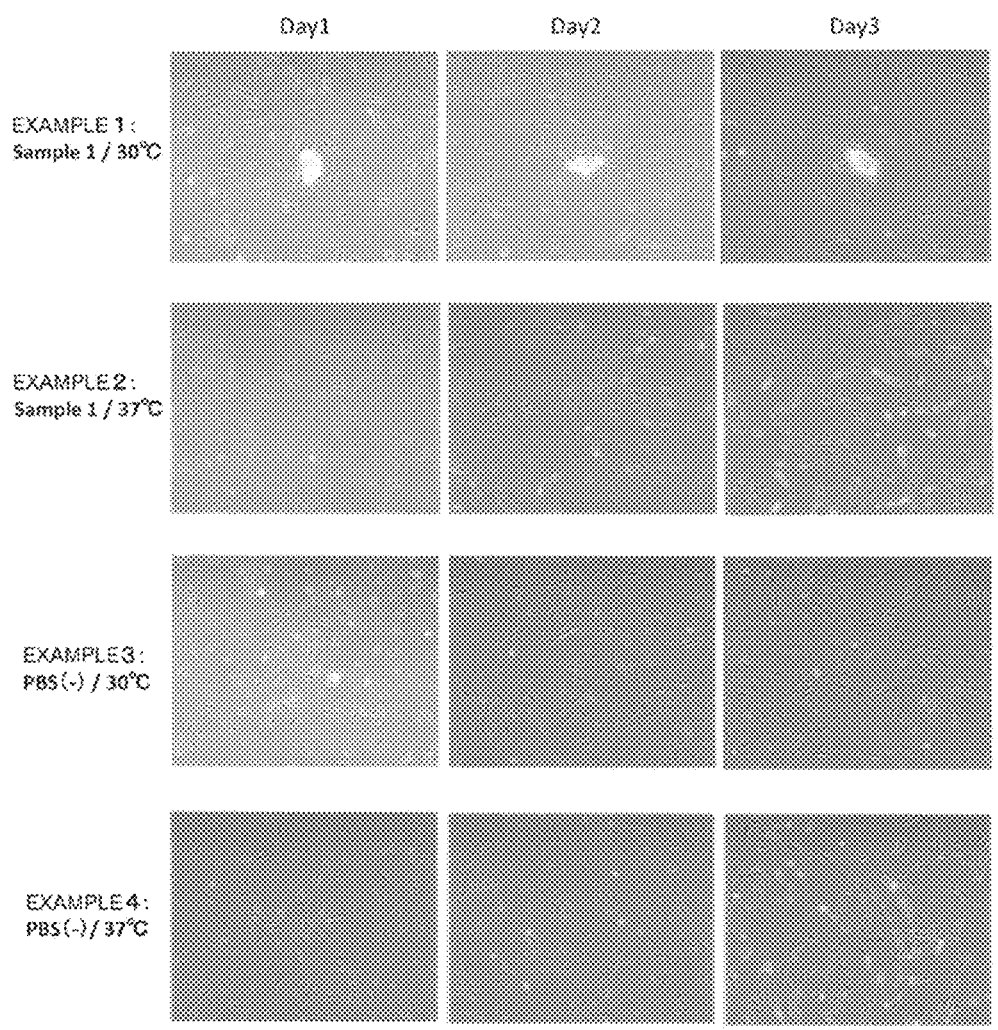
FIG. 1 contains optical micrographs (images) that show the morphology of fibroblasts that have been cultured under different cell culture temperature conditions and different conditions of addition of a reprogramming-inducing peptide (sample 1) according to a working example, wherein in each instance images are given for observation on the 1st, 2nd, and 3rd days after the start of culture.

Preferred embodiments of the present invention are described below. In addition to those matters that are particularly described in this Description (for example, the primary structure and chain length of the herein disclosed synthetic peptide), those matters required for the execution of the present invention but not particularly described in this Description (for example, methods for the chemical synthesis of the peptide, cell culture techniques, general matters relating to the preparation of a pharmaceutical composition having a peptide as a component) can be understood as design matters for the individual skilled in the art based on the conventional art in the fields of, for example, cell engineering, physiology, medicine, pharmacy, organic chemistry, biochemistry, genetic engineering, protein engineering, molecular biology, and genetics. The present invention can be implemented based on the contents disclosed in this Description and the common general technical knowledge in these fields. Depending on the case, in the following description the amino acids are given by one-letter symbols in conformity with the amino acid nomenclature given in the IUPAC-IUB guidelines (however, the three-letter designations are used in the sequence listings).

The content of each literature cited in this Description is incorporated in its entirety in this Description by reference.

In this Description, "synthetic peptide" refers to a peptide fragment whose peptide chain as such does not exist independently in a stable manner in nature, but rather is produced by artificial chemical synthesis or biosynthesis (that is, production based on genetic engineering) and can exist in a stable manner in a prescribed composition (for example, in a carrier such as physiological saline).

Also in this Description, "peptide" is a term that indicates an amino acid polymer that has a plurality of peptide bonds and, while there is no limitation on the number of amino acid residues that may be present in the peptide chain, this term typically refers to a relatively low molecular weight wherein the total number of amino acid residues is not more than about 100 (preferably not more than 60 and particularly preferably not more than 50, for example, not more than 30).

Also in this Description, "amino acid residue" is a term that includes, unless specifically indicated otherwise, the N-terminal amino acid and C-terminal amino acid of the peptide chain.

The amino acid sequences described in this Description always have the N-terminal side for the left side and the C-terminal side for the right side.

In this Description, a "modified amino acid sequence" refers, with respect to a particular amino acid sequence, to an amino acid sequence formed by the substitution, deletion, and/or addition (insertion) of 1 or a plurality of amino acid residues, for example, 1, 2, or 3 amino acid residues, but without the loss of the function exhibited by the particular amino acid sequence (for example, the reprogramming-inducing activity exhibited by the aforementioned reprogramming-inducing peptide or the membrane permeation capacity exhibited by the membrane-permeable peptide described below). Typical examples that are encompassed by the modified amino acid sequences referenced by this Description include, for example, the following: sequences produced by what is known as conservative amino acid replacement, in which conservative substitution by 1, 2, or 3 amino acid residues is carried out (for example, a sequence in which a basic amino acid residue is replaced by another basic amino acid residue: for example, exchange between the lysine residue and the arginine residue), and sequences obtained by the addition (insertion) to a particular amino acid sequence or deletion from a particular amino acid sequence of 1, 2, or 3 amino acid residues. Accordingly, the herein disclosed reprogramming-inducing peptide encompasses synthetic peptides constituted of an amino acid sequence that is the same as an amino acid sequence according to the SEQ ID NOs, but also encompasses synthetic peptides formed of an amino acid sequence obtained by the substitution (for example, the aforementioned conservative amino acid replacement), deletion, and/or addition of 1, 2, or 3 amino acid residues in an amino acid sequence given by a SEQ ID NO, wherein these amino acid sequences exhibit the same or a similar reprogramming-inducing activity.

In this Description, a "differentiated cell" denotes any cell that has undergone differentiation from an undifferentiated cell. This is typically synonymous with somatic cells. That is, this includes not only terminally differentiated cells, but also various somatic stem cells and precursor cells. Examples here are stem cells that lack pluripotency (including precursor cells), e.g., endodermal cells, mesodermal cells, ectodermal cells, mesenchymal stem cells, hematopoietic stem cells, and neural stem cells; white blood cells, red blood cells, and neural cells (neurons); and terminally differentiated cells such as muscle cells, liver cells, and pancreatic cells.

In this Description, "reprogramming" refers to making a differentiated cell into a cell in an undifferentiated state. Here, whether a cell is in an undifferentiated state can be evaluated based on the expression of an undifferentiated marker gene (typically the presence of the particular protein that is a gene product of this gene) that is known to be specifically expressed in a pluripotent stem cell (ES cell or iPS cell), which is an undifferentiated cell. Undifferentiated marker genes can be exemplified by the endogenous Oct3/4, Nanog, Sox2, TRA1-81, TRA1-60, SSEA-1, SSEA-3, SSEA-4, and alkaline phosphatase (ALP). That is, in this Description, "undifferentiated cell" refers to a cell that expresses at least one of the undifferentiated marker genes (expresses the protein that is the gene product of the particular gene) among the heretofore known undifferentiated marker genes. Typically this refers to a cell that expresses at least 1 (preferably at least 2 and more preferably at least 3) gene selected from the group of the endogenous Oct3/4, Nanog, Sox2, TRA1-81, TRA1-60, SSEA-1, SSEA-3, SSEA-4, and alkaline phosphatase (ALP). It can be, for example, a cell that expresses at least Oct3/4 and Nanog.

The herein disclosed reprogramming-inducing peptide is a synthetic peptide (i.e., a reprogramming-inducing peptide) discovered for the first time by the present inventors to exhibit—when supplied to the cell culture (typically by addition to the medium in which the cells are being cultured) of a particular differentiated cell (typically a cell of human origin, or non-human mammal origin, or avian origin, or from some other animal)—the capacity of being able to reprogram the cell, i.e., to exhibit a reprogramming-inducing activity. In addition, the herein disclosed reprogramming-inducing agent is a composition (pharmaceutical composition) used to induce the reprogramming of a target differentiated cell and characteristically contains at least one species of the aforementioned reprogramming-inducing peptide as an effective component (that is, a substance that participates in the reprogramming of a target differentiated cell).

As indicated above, the herein disclosed reprogramming-inducing peptide is a synthetic peptide that contains, as a reprogramming-inducing peptide sequence, the following amino acid sequence:

(SEQ ID NO: 1)
CKSKSRRSC or a modified amino acid sequence therefrom. The specific amino acid sequence given in SEQ ID NO: 1 is an artificial amino acid sequence having a total of 9 amino acid residues and obtained when the present inventors on their own translated an RNA sequence constituting siRNA for centrin 2 of human origin and is also an amino acid sequence discovered for the first time by the present inventors to have the ability to induce the reprogramming of a differentiated cell.

This centrin is a centrosome-associated protein that is present in the centrosome of eukaryotic cells and, as a constituent protein of the centriole, is involved with centriole replication and microtubule cleavage, and centrin 2 is a protein belonging to the centrin family (typically centrin 1, centrin 2, centrin 3, and so forth) (refer to Non Patent Literature 4).

Alternatively, the herein disclosed reprogramming-inducing peptide may be a peptide formed of the reprogramming-inducing peptide sequence described above, or, in order to efficiently introduce the reprogramming-inducing peptide sequence into the cell, it may have a membrane-permeable peptide sequence at the N-terminal side or C-terminal side of the reprogramming-inducing peptide sequence. Any amino acid sequence that constitutes a membrane-permeable peptide that can pass through the cell membrane and/or nuclear membrane can be used as this membrane-permeable peptide sequence without particular limitation. Numerous suitable membrane-permeable peptide sequences are known, but in particular an amino acid sequence (or a modified amino acid sequence therefrom) associated with a nucleolar localization signal (NoLS) is preferred for the amino acid sequence of the membrane-permeable peptide sequence of the reprogramming-inducing peptide. Advantageous examples of NoLS-associated membrane-permeable peptide sequences and other membrane-permeable peptide sequences are given in SEQ ID NOs: 2 to 6. The specifics are given in the following.

Thus, the amino acid sequence in SEQ ID NO: 2 corresponds to an NoLS formed of a total of 13 amino acid residues from the 491st amino acid residue to the 503rd amino acid residue of the LIM kinase 2 present in human endothelial cells, which is a type of protein kinase involved with intracellular signal transduction.

The amino acid sequence in SEQ ID NO: 3 corresponds to an NoLS formed of a total of 8 amino acid residues contained in the nucleocapsid (N) protein of avian infectious bronchitis virus (IBV).

The amino acid sequence of SEQ ID NO: 4 corresponds to a membrane-permeable peptide sequence formed of a total of 1 amino acid residues derived from the protein transduction domain contained in TAT of human immunodeficiency virus (HIV).

The amino acid sequence of SEQ ID NO: 5 corresponds to a membrane-permeable peptide sequence formed of a total of 11 amino acid residues of a modified-TAT protein transduction domain (PTD4).

The amino acid sequence of SEQ ID NO: 6 corresponds to a membrane-permeable peptide sequence formed of a total of 16 amino acid residues derived from ANT of Antennapedia, a *Drosophila* mutant.

The membrane-permeable peptide sequences given in the sequence listings are given entirely by way of example, and usable peptide sequences are not limited to these. Various membrane-permeable peptide sequences usable for the execution of the present invention are described in numerous publications that had been published at the time of filing of this application. The amino acid sequences of these membrane-permeable peptide sequences can be readily acquired by common search means.

In particular, the amino acid sequence shown in SEQ ID NO: 2 (or modified amino acid sequence therefrom), which is also described in Patent Literature 2, is preferred for the membrane-permeable peptide sequence. A synthetic peptide exhibiting a high reprogramming-inducing activity can be obtained by combining the amino acid sequence given in SEQ ID NO: 2 with a reprogramming-inducing peptide sequence (SEQ ID NO: 1) as described above.

The peptide chain (amino acid sequence) of the herein disclosed reprogramming-inducing peptide can in some cases be constructed by combining the reprogramming-inducing peptide sequence as described above with a membrane-permeable peptide sequence as appropriate. In relational terms, either of the reprogramming-inducing peptide sequence and membrane-permeable peptide sequence may be located at the C-terminal side (N-terminal side). In addition, the reprogramming-inducing peptide sequence is preferably located adjacent to the membrane-permeable peptide sequence. That is, either an amino acid residue not belonging to these two sequences is not present between the reprogramming-inducing peptide sequence and the membrane-permeable peptide sequence, or, if present, the number of such residues is preferably about 1 to 3. For example, 1 or a plurality (typically 2 or 3) of amino acid residues (for example, 1 or a plurality of glycine (G) residues) that function as a linker may be incorporated between the reprogramming-inducing peptide sequence and the membrane-permeable peptide sequence.

The herein disclosed reprogramming-inducing peptide can be one in which at least one of the amino acid residues is amidated. The amidation of the carboxyl group in an amino acid residue (typically the C-terminal amino acid residue of the peptide chain) can improve the structural stability (for example, the resistance to protease) of a synthetic peptide.

In addition, the herein disclosed reprogramming-inducing peptide may contain, insofar as its reprogramming-inducing activity is not impaired, a sequence (amino acid residue) portion other than the amino acid sequences that constitute the reprogramming-inducing peptide sequence and membrane-permeable peptide sequence. While there is no particular limitation thereon, this partial amino acid sequence is preferably a sequence that can maintain the three-dimensional shape (typically a linear shape) of the reprogramming-inducing peptide sequence and membrane-permeable peptide sequence portion.

There are no particular limitations on the conformation (steric structure) of the reprogramming-inducing peptide as long as it can exhibit a reprogramming-inducing activity in the environment of use (in vitro or in vivo). However, a linear or helical shape is preferred from the standpoint of resistance to becoming an immunogen (antigen). It is difficult for a peptide with such a shape to constitute an epitope. There are no particular limitations on the number of amino acid residues that constitute the peptide chain of the reprogramming peptide, but a short-chain peptide is preferred viewed from the perspective of ease of chemical synthesis and the ability to inexpensively provide the reprogramming-inducing peptide. Such a short-chain peptide typically has a high structural stability (for example, resistance to protease) and excellent handling properties and an excellent storability. Viewed from this perspective, the reprogramming-inducing peptide is suitably linear and has a relatively low molecular weight (typically not more than 50 amino acid residues and preferably not more than 30 amino acid residues, for example, not more than 25 amino acid residues). For example, it may be a synthetic peptide having not more than 10 amino acid residues. A short-chain peptide formed of only the amino acid sequence with SEQ ID NO: 1 is a preferred example.

The proportion taken up by the reprogramming-inducing peptide sequence and membrane-permeable peptide in the total amino acid sequence (peptide chain), i.e., the number % for the number of amino acid residues that constitute the reprogramming-inducing peptide sequence and membrane-permeable peptide sequence with reference to the total number of amino acid residues that constitute the peptide chain, is not particularly limited insofar as the reprogramming-inducing activity is not impaired; however, this proportion is desirably at least about 60%, preferably at least 80%, and particularly preferably at least 90%. A peptide formed of the reprogramming-inducing peptide sequence and the membrane-permeable peptide sequence (that is, these sequences are 100% of the total amino acid sequence, or, when a linker of 1 to several amino acid residues is present, these sequences account for everything other than the linker) is a preferred embodiment.

When the peptide chain does not have a membrane-permeable peptide sequence, the proportion for the reprogramming-inducing peptide sequence in the total amino acid sequence is then desirably at least about 60%, preferably at least 80%, and particularly preferably at least 90%. A peptide formed of the reprogramming-inducing peptide sequence (i.e., the reprogramming-inducing peptide sequence accounts for 100% of the total amino acid sequence) is a preferred example.

All of the amino acid residues in the reprogramming-inducing peptide of the present invention are preferably L-amino acids, but, insofar as the reprogramming-inducing activity is not impaired, all or a portion of the amino acid residues may be replaced by D-amino acids.

The herein disclosed reprogramming-inducing peptide can be readily produced in conformity with common methods of chemical synthesis. For example, a heretofore known solid-phase synthetic method or liquid-phase synthetic method may be used. A solid-phase synthetic method using Boc (t-butyloxycarbonyl) or Fmoc (9-fluorenylmethoxycarbonyl) as the protective group for the amino group is advantageous.

A peptide chain having the desired amino acid sequence and modifications (C-terminal amidation and so forth) can be synthesized for the herein disclosed reprogramming-inducing peptide using a solid-phase method using a commercially available peptide synthesizer (available, for example, from Intavis AG or Protein Technologies, Inc.).

Or, the reprogramming-inducing peptide may be biosynthesized based on a genetic engineering procedure. That is, a polynucleotide (typically DNA) is synthesized that has a nucleotide sequence (including the ATG start codon) that encodes the amino acid sequence of the desired reprogramming-inducing peptide. A recombinant vector is then constructed in conformity with the host cell; this recombinant vector has an expressible gene construct formed of the synthesized polynucleotide (DNA) and various regulatory elements (including a promoter, ribosome binding site, terminator, enhancer, and various cis elements that control the expression level) supporting expression of the amino acid sequence in the host cell.

Using common procedures, this recombinant vector is introduced into a prescribed host cell (for example, yeast, insect cell, animal cell) and this host cell, or tissue or specimen containing this cell, is cultured under prescribed conditions. By doing this, the target peptide can be expressed and produced within the cell. The peptide is isolated from the host cell (or medium in the case of secretion), and the target reprogramming-inducing peptide can be obtained by carrying out refolding, purification, and so forth as necessary.

Methods heretofore employed in this field may be used as such for the method for constructing the recombinant vector, the method for introducing the constructed recombinant vector into the host cell, and so forth, and, since these methods are not themselves particular characteristic features of the present invention, a detailed description thereof is omitted.

For example, a fusion protein expression system can be used to bring about the efficient production of large amounts within the host cell. That is, a gene (DNA) encoding the amino acid sequence of the target reprogramming-inducing peptide is chemically synthesized, and the synthesized gene is introduced into a suitable site in a suitable fusion protein expression vector (for example, glutathione S-transferase (OST) fusion protein expression vectors such as the pET series from Novagen Inc and the pGEX series from Amersham Biosciences). The host cell (typically *E. coli*) is transformed with this vector. The resulting transformant is cultured to produce the target fusion protein. This protein is then extracted and purified. The obtained purified fusion protein is subsequently cleaved with a prescribed enzyme (protease) and the liberated target peptide fragment (the designed reprogramming-inducing peptide) is recovered using a method such as affinity chromatography. As necessary, refolding is performed using a suitable method. The herein disclosed reprogramming-inducing peptide can be produced using such a heretofore known fusion protein expression system (for example, the GST/His system from Amersham Biosciences can be used).

Alternatively, a template DNA (i.e., a synthetic gene fragment containing a nucleotide sequence that encodes the amino acid sequence of the reprogramming-inducing peptide) for a cell-free protein synthesis system is constructed, and, using the various compounds (ATP, RNA polymerase, amino acids, and so forth) required for peptide synthesis, an in vitro synthesis of the target polypeptide can be carried out using what is known as a cell-free protein synthesis system. Reference is made to the reports of Shimizu et al. (Shimizu et al., Nature Biotechnology, 19, 751-755 (2001)) and Madin et al. (Madin et al., Proc. Natl. Acad. Sci. USA, 97(2), 559-564 (2000)) for cell-free protein synthesis systems. At the time of filing of this application, numerous firms were already engaged in contract polypeptide production based on the technology described in these reports; kits for cell-free protein synthesis are also commercially available (for example, the PROTEIOS (trademark) wheat germ cell-free protein synthesis kit available from CellFree Sciences Co., Ltd. (Japan)).

A single-strand or double-strand polynucleotide containing a nucleotide sequence encoding the herein disclosed reprogramming-inducing peptide and/or a nucleotide sequence complementary to this sequence can be readily produced (synthesized) by heretofore known methods. Thus, by selecting the codons that correspond to the individual amino acid residues constituting the intended amino acid sequence, a nucleotide sequence corresponding to the amino acid sequence of the reprogramming-inducing peptide can be easily determined and provided. Once the nucleotide sequence has been determined, a polynucleotide (single strand) corresponding to the desired nucleotide sequence can be readily obtained using, for example, a DNA synthesizer. Then, using the obtained single-strand DNA as a template, the target double-strand DNA can be obtained using various enzymatic synthesis procedures (typically PCR). In addition, the polynucleotide may take the form of DNA or RNA (for example, mRNA). The DNA can be provided in double strand or single strand form. When provided in single strand form, it may be the coding strand (sense strand) or may be the noncoding strand (antisense strand) with a sequence complementary thereto.

As noted above, the thusly obtained polynucleotide can be used as a starting material for the construction of a recombinant gene (expression cassette) for producing the reprogramming-inducing peptide in various host cells or in a cell-free protein synthesis system.

Insofar as the reprogramming-inducing activity is not impaired, the herein disclosed reprogramming-inducing peptide may take the form of a salt. For example, an acid-addition salt of the peptide can be used, which can be obtained by an addition reaction according to the usual methods of a commonly used inorganic acid or organic acid. Or, it may take another salt form (for example, a metal salt) insofar as the reprogramming-inducing activity is exhibited. Accordingly, the "peptide" referenced in this Description and in the claims also encompasses peptides in these salt forms.

Insofar as the reprogramming-inducing peptide effective component can be kept in a state in which its reprogramming-inducing activity is not impaired, the herein disclosed reprogramming-inducing agent may contain any of various pharmaceutically (medicinally) acceptable carriers in correspondence to the form of use. The carriers commonly used in peptide drugs as, e.g., diluents, excipients, and so forth, are preferred. While the carrier can vary as appropriate in correspondence to the application and form of the reprogramming-inducing agent, typical examples are water, physiological buffers, and various organic solvents. It can be an aqueous alcohol (e.g., ethanol) solution of suitable concentration, glycerol, or a nondrying oil such as olive oil. Or it may be a liposome. Examples of secondary components that can be incorporated in the reprogramming-inducing agent are various fillers, extenders, binders, moisturizers, surfactants, colorants, fragrances, and so forth.

There are no particular limitations on the form of the reprogramming-inducing agent. Specific forms can be exemplified by solutions, suspensions, emulsions, aerosols, foams, granules, powders, tablets, capsules, ointments, and aqueous gels. It can also be made as a lyophilizate or granulate for preparation of a drug solution by dissolution in, for example, physiological saline or an appropriate buffer (for example, PBS), immediately before use.

The processes as such that are used to prepare the various drug (composition) forms using the reprogramming-inducing peptide (main component) and various carriers (secondary component) as starting materials may conform to heretofore known methods, and these formulation methods are not themselves characteristic features of the present invention and a detailed description thereof is therefore omitted. A source of detailed information on formulation is, for example, Comprehensive Medicinal Chemistry, edited by Corwin Hansch. Pergamon Press (1990). The contents of this publication are incorporated in their entirety in this Description by reference.

The differentiated cells to which the reprogramming-inducing peptide (reprogramming-inducing agent) may be applied are not particularly limited, and various differentiated cells can be reprogrammed using this reprogramming-inducing peptide (reprogramming-inducing agent). Examples here are cells of human origin or non-human animal origin (typically vertebrates and particularly mammals). In particular, cells of human origin, because of their high utility in the field of medical science, are preferred for the target cell. For example, cells originating from tissues such as the skin, blood, teeth, mucous membranes, and so forth are preferred because they can be collected in a minimally invasive manner without substantial damage to the living organism. Viewed from the standpoint of ease of culture (maintenance) using in vitro culture systems, fibroblasts, which have a high proliferative capacity and typically can be monocultured, are preferred as the target cell. Fibroblasts are cells that are present mainly in connective tissue and can be collected from any tissue in the body. For example, fibroblasts from tissues such as the skin (dermis), digestive tract, blood vessels, bone, teeth, cartilage, brain, eye, lung, and so forth can be used. Among these preferred target cells, fibroblasts of human skin origin and human blood cells are preferred application targets from the standpoint of the ease of collection from the body (low invasiveness) and the ease of culture (maintenance) using in vitro culture systems.

The herein disclosed reprogramming-inducing peptide (or reprogramming-inducing agent containing this peptide) can be used according to a method and in a dose in conformity with its form and the objective.

For example, when reprogramming is to be carried out on a differentiated cell that is being cultured (subcultured) outside the organism (in vitro), a suitable amount of the herein disclosed reprogramming-inducing peptide (or reprogramming-inducing agent containing this peptide) may be supplied at least once, to the target differentiated cell to be reprogrammed (cell culture), to the medium at any stage in the culture process (preferably at the same time as the start of culture or soon after the start of culture). The amount supplied and the number of times of supply are not particularly limited because these can vary with such conditions as the type of cell being cultured, the cell density (cell density at the start of culture), the number of passages, the culture conditions, the type of medium, and so forth. When a differentiated cell of mammal origin (typically a differentiated cell of human origin) is to be reprogrammed, supply to the cultured cell (cell culture) is preferably carried out once or a plurality of times (for example, at the start of culture with supplementary supply with subculture of the cell or medium exchange) so as to provide a reprogramming-inducing peptide concentration in the medium in the range of about 0.1 µM to 100 µM and preferably in the range of 0.5 µM to 50 µM (for example, 1 µM to 20 µM).

The reprogramming-inducing peptide (reprogramming-inducing agent) can induce the reprogramming of a differentiated cell without requiring other reprogramming factors (for example, genes such as Oct3/4, klf4, c-Myc, and Sox2 and their gene products). However, the reprogramming-inducing peptide (reprogramming-inducing agent) may be used in combination with heretofore known reprogramming factors for the purpose of, for example, increasing the reprogramming efficiency in cell culture. Various means for iPS production other than reprogramming factors—for example, use of a differentiation inhibitor (also referred to as an undifferentiation maintenance factor, for example, leukemia inhibitory factor (LIF) and basic fibroblast growth factor (bFGF)) or a reprogramming promoter (for example, protein kinase C inhibitor (PKC inhibitor) and TGF-β signaling inhibitor), use of feeder cells (for example, MEF cells, SNL cells), a coating treatment of the culture chamber (for example, a Matrigel coating treatment)—can be applied without particular limitation when the present invention is carried out.

The herein disclosed method for producing an undifferentiated cell (that is, a method for reprogramming a target differentiated cell) is a method that includes preparing a cell culture that contains a target differentiated cell; supplying the reprogramming-inducing peptide (or reprogramming-inducing agent containing this peptide) to the cell culture; and culturing the cell culture to which the reprogramming-inducing peptide has been supplied and thereby inducing the reprogramming of the target cell.

The method for preparing the cell culture containing the target differentiated cell is not particularly limited, and heretofore known methods can be used as appropriate, for example, culture methods for primary cell cultures and culture methods for cell lines. The method for preparing the cell culture is not itself a characteristic feature of the present invention and a detailed description thereof is therefore omitted.

The same conditions as for the ordinary culture of the target differentiated cell can be used for the culture conditions for culturing the cell culture to which the reprogramming-inducing peptide has been supplied. For example, with regard to the culture temperature, when an undifferentiated cell is to be produced by reprogramming a differentiated cell of mammal origin, the usual culture temperature for the differentiated cell of mammal origin can be used. The optimal temperature condition can vary with, for example, the type and condition of the target differentiated cell; however, in the typical case in which the cell is of mammal origin, the optimal temperature condition can be established as appropriate in the temperature range of, for example, at least 25° C. and less than 37° C. (preferably at least 25° C. and not more than 35° C. and more preferably at least 30° C. and not more than 35° C.). The following can be used without particular limitation as the medium used for the culture: media with the same composition as for the ordinary culture of the target differentiated cell, or media with the same composition as the media commonly used for the production of iPS cells. With regard to the humidity and $CO_2$ concentration in the incubator, the same conditions as for the ordinary culture of the target differentiated cell (for example, 5% $CO_2$, relative humidity of at least 95%) can be used without particular limitation.

The culture time for the cell culture that has been supplied with the reprogramming-inducing peptide should be a time that enables induction of target cell reprogramming to occur, but is not otherwise particularly limited. For example, culture may be carried out for at least 1 day, preferably at least 3 days, and more preferably at least 7 days. The induction of reprogramming of the target differentiated cell can generally be carried out within 35 days (preferably within 28 days and more preferably within 21 days, for example, within 14 days).

The herein disclosed method for producing an undifferentiated cell may also include selecting (separating) the undifferentiated cell from the cell culture that has been cultured after the supply of the reprogramming-inducing peptide. Doing this enables the production of an undifferentiated cell population (cell culture containing this cell population) that has a high proportion (purity) for the undifferentiated cell count in the total cell count.

For example, methods for selecting (separating) undifferentiated iPS cells from within a cell culture that contains iPS cells can be used without particular limitation as the method for selecting (separating) undifferentiated cells from the cell culture containing undifferentiated cells. For example, selection can be carried out in such a selection method by using a suitable selection medium, collecting (picking up) cells that constitute a cluster under a microscope, and carrying out cell selection (cell sorting, for example, sorting using FACS) based on the status of expression of an undifferentiated marker gene (typically the presence of protein that is the gene product of this gene).

Whether reprogramming of the differentiated cell has been induced by the execution of the present method, i.e., whether cells produced by the execution of the present method are cells in an undifferentiated state, can be evaluated by confirmation of the expression (typically the expression of the protein that is the gene product of the gene) of at least 1 (preferably at least 2 and more preferably at least 3) of the genes (endogenous genes) used as undifferentiated marker genes for pluripotent stem cells (for example, ES cells, iPS cells). The heretofore known undifferentiated marker genes can be used without particular limitation, such as, for example, endogenous Oct3/4, Nanog, Sox2, TRA1-81, TRA1-60, SSEA-1, SSEA-3, SSEA-4, and alkaline phosphatase (ALP).

Viewed from the standpoint of improving the accuracy of the evaluation, the expression of a plurality of undifferentiated marker genes is preferably confirmed. The expression of at least Oct3/4 and Nanog is preferred; the expression, besides Oct3/4 and Nanog, of at least one undifferentiated marker gene selected from Sox2, TRA1-81, SSEA-3, and ALP is more preferred; and the expression of Oct3/4, Nanog, Sox2, TRA1-81, SSEA-3, and ALP is still more preferred.

The expression of an undifferentiated marker gene can be confirmed, for example, by detecting the presence of the mRNA or protein that is a gene product of the gene using a common molecular biological procedure, e.g., a procedure using an enzyme reaction or an immunological procedure using an antibody-antigen reaction, and specifically using a procedure such as a quantitative reverse transcriptase-polymerase chain reaction (qPCR), western blotting, cytoimmunostaining, and so forth.

Alternatively, because reprogrammed cells typically form clusters with a morphology resembling the clusters (cell aggregates, colonies) that are formed by pluripotent stem cells (for example, ES cells, iPS cells), i.e., pluripotent stem cell-like clusters (ES cell-like clusters or iPS cell-like clusters), reprogrammed cells may also be confirmed by observation of the cell morphology using a microscope (e.g., phase contrast microscope, differential interference microscope).

In the following, an undifferentiated cell produced using the herein disclosed reprogramming-inducing peptide is referred to as a short peptide-induced reprogramming, undifferentiated stage cell (SIRIUS cell). By inducing the differentiation of undifferentiated cells (SIRIUS cells) produced by the herein disclosed method for producing undifferentiated cells, the present inventors have confirmed that these SIRIUS cells can be differentiated into a desired differentiated cell (including a cell mass, tissue, organ, and so forth), i.e., that SIRIUS cells possess pluripotency. Heretofore known methods for inducing differentiation can be adapted without particular limitation as methods for causing the differentiation of SIRIUS cells. These methods for inducing the differentiation of SIRIUS cells are not themselves characteristic features of the present invention and a detailed description thereof is therefore omitted.

SIRIUS cells can be advantageously used as materials in regenerative medicine (typically a cell resource used for the production of cells for transplantation). For example, repair or regeneration at an affected site (i.e., within the body of a patient) requiring repair or regeneration can be effectively carried out by returning to the affected site differentiated cells (including a cell mass, tissue, organ, and so forth) produced by inducing the differentiation of SIRIUS cells outside the body (in vitro) or returning a biosynthetic product from such cells. That is, various diseases can be efficiently treated in a therapeutic method in which the regeneration of tissue structures has a prominent role. The biosynthetic products derived from differentiated cells produced by inducing the differentiation of SIRIUS cells can be exemplified by physiologically active substances such as secreted proteins and hormones (for example, insulin).

Differentiated cells produced by inducing the differentiation of SIRIUS cells can also be advantageously used in the evaluation of the toxicity and efficacy (for example, the drug efficacy) of drugs, compounds, natural extracts, poisons, and so forth. This then enables the evaluation to be carried out at lower costs and in a more stable manner than for conventional evaluation methods using, for example, test animals or primary cell cultures.

In addition, SIRIUS cells of human origin (for example, patient-derived SIRIUS cells and particularly patient-derived SIRIUS cells where the disease is due to genetic factors) can be advantageously used, for example, for research and development in the areas of disease pathogenesis and drug therapies and thus have high utility as research target cells in these areas of research.

Several working examples pertaining to the present invention are described below, but this does not mean that the present invention is limited to or by what is shown in these working examples.

Working Example 1: Peptide Synthesis

For the reprogramming-inducing peptide, a peptide formed of the reprogramming-inducing peptide sequence of CKSKSRRSC (SEQ ID NO: 1) was synthesized using a commercial peptide synthesizer (product of Intavis AG) and using a solid-phase synthesis method (Fmoc method) according to the manual. This linear synthetic peptide formed of a total of 9 amino acid residues is referred to as "sample 1" in the following.

The mode of use of the peptide synthesizer is not itself a characteristic feature of the present invention and a detailed description thereof is therefore omitted. The synthesized sample 1 was dissolved in PBS (−) to prepare a peptide stock solution.

Working Example 2: Production of SIRIUS Cells

SIRIUS cells were produced using the sample 1 obtained in Working Example 1. CCD1079SK cells (ATCC (registered trademark) CRL-2097), which are a fibroblast cell culture line derived from human skin tissue, were used as the sample cells. The details of the tests are as follows.

The CCD1079SK cells, which had been stored frozen, were inoculated to six culture dishes with a diameter of 60 mm (60 mm dishes) to provide a cell density of $3 \times 10^5$ cells/well. Specifically, the thawed CCD1079SK cells were first suspended in ordinary Dulbecco's modified Eagle's medium (DMEM medium) to produce a cell suspension having a cell density of $1.5 \times 10^5$ cells/mL and 2 mL of this cell suspension was introduced into the 60 mm dish. This DMEM medium contained 10% FBS, 100 units/mL of penicillin, and 100 μg/mL of streptomycin in ordinary DMEM (Wako Pure Chemical Industries, Ltd., Cat. No. 043-30085).

The CCD1079SK cells inoculated into the 60 mm dish were precultured for several hours (approximately 6 hours) in an incubator under conditions of 5% $CO_2$ and 37° C.

After the preculture for several hours, the CCD1079SK cells were subjected to a main culture at one of the culture conditions indicated for examples 1 to 6 in Table 1. The specific culture conditions are given in the following.

The culture conditions according to example 1 are as follows: the stock solution of sample 1 is added, in an amount that provides a peptide concentration in the medium of 20 μM, to the DMEM medium (in the 60 mm dish) on which the CCD1079SK cells are being cultured, and culture is carried out under a temperature condition of 30° C.

The culture conditions according to example 2 are as follows: the stock solution of sample 1 is added, in an amount that provides a peptide concentration in the medium of 20 μM, to the DMEM medium (in the 60 mm dish) on which the CCD1079SK cells are being cultured, and culture is carried out under a temperature condition of 37° C.

The culture conditions according to example 3 are as follows: PBS (−) is added, in the same volume as for the peptide stock solution added to the sample 1 addition group, to the DMEM medium (in the 60 mm dish) on which the CCD1079SK cells are being cultured, and culture is carried out under a temperature condition of 30° C.

The culture conditions according to example 4 are as follows: PBS (−) is added, in the same volume as for the peptide stock solution added to the sample 1 addition group, to the DMEM medium (in the 60 mm dish) on which the CCD1079SK cells are being cultured, and culture is carried out under a temperature condition of 37° C.

The culture conditions according to example 5 are as follows: the stock solution of sample 1 is added, in an amount that provides a peptide concentration in the medium of 20 μM, to the DMEM medium (in the 60 mm dish) on which the CCD1079SK cells are being cultured, and culture is carried out under a temperature condition of 13° C.

The culture conditions according to example 6 are as follows: the stock solution of sample 1 is added, in an amount that provides a peptide concentration in the medium of 20 μM, to the DMEM medium (in the 60 mm dish) on which the CCD1079SK cells are being cultured, and culture is carried out under a temperature condition of 22° C.

Other than the culture temperature and the presence/absence of peptide addition, the same culture conditions were used in all of examples 1 to 6. Thus, in all of examples 1 to 6, culture was carried out in a 5% $CO_2$ atmosphere using a DMEM medium with the same composition (same as that used in the preculture). In addition, in all of examples 1 to 6, culture exchange and peptide addition (addition of PBS (−) in the peptide-free groups) were carried out every two days after the start of the main culture.

TABLE 1

| example | peptide addition status | culture temperature |
|---------|------------------------|--------------------|
| 1 | sample 1 addition (20 μM) | 30° C. |
| 2 | sample 1 addition (20 μM) | 37° C. |
| 3 | no peptide addition | 30° C. |
| 4 | no peptide addition | 37° C. |
| 5 | sample 1 addition (20 μM) | 13° C. |
| 6 | sample 1 addition (20 μM) | 22° C. |

Observation of the cell morphology using a phase-contrast microscope was carried out in each example on the 1st, 2nd, 3rd, 4th, 5th, 6th, 7th, 9th, 13th, 21st, 27th, and 34th days after the start of the main culture (cell culture in the presence of peptide). The micrographs (images) obtained by this microscopic observation are given in FIGS. 1 to 5 and FIG. 7. Among the images in FIG. 2, the micrographs given for example 3 are micrographs (images) showing cell aggregates (clusters) that were rarely identified when tests were independently repeated a plurality of times using the same conditions as in example 3.

As shown in FIG. 1, the formation of aggregates (clusters) of aggregated cells was found in the culture of example 1 within 3 days after the start of the main culture (typically 1 day after the start of the main culture (after approximately 24 hours)) under the indicated conditions. The morphology of the clusters was found to be a morphology very similar to the morphology of clusters (colonies) of pluripotent stem cells (ES cells or iPS cells and particularly ES cells).

When tests were independently repeated a plurality of times using the same conditions as in example 1, it was found that at least 1 cluster was formed in the 60 mm dish at a probably of at least 95% (26 times in 27 tests) within the 3rd day after the start of culture in the presence of the peptide. In this case, the number (frequency) of clusters formed per one 60 mm dish was an average of 3.

On the other hand, as shown in FIG. 1, cell aggregates (clusters) did not form, or their formation frequency was very low, in the cultures in examples 2 to 4 within 3 days after the start of the main culture. Tests under the same conditions as in examples 2 to 4 were independently repeated a plurality of times and the morphology of the rarely identified cell aggregates (clusters) were observed in detail: the cell aggregation conditions were looser than for the clusters observed in example 1 and the edges of the clusters were indistinct.

Figure 7:
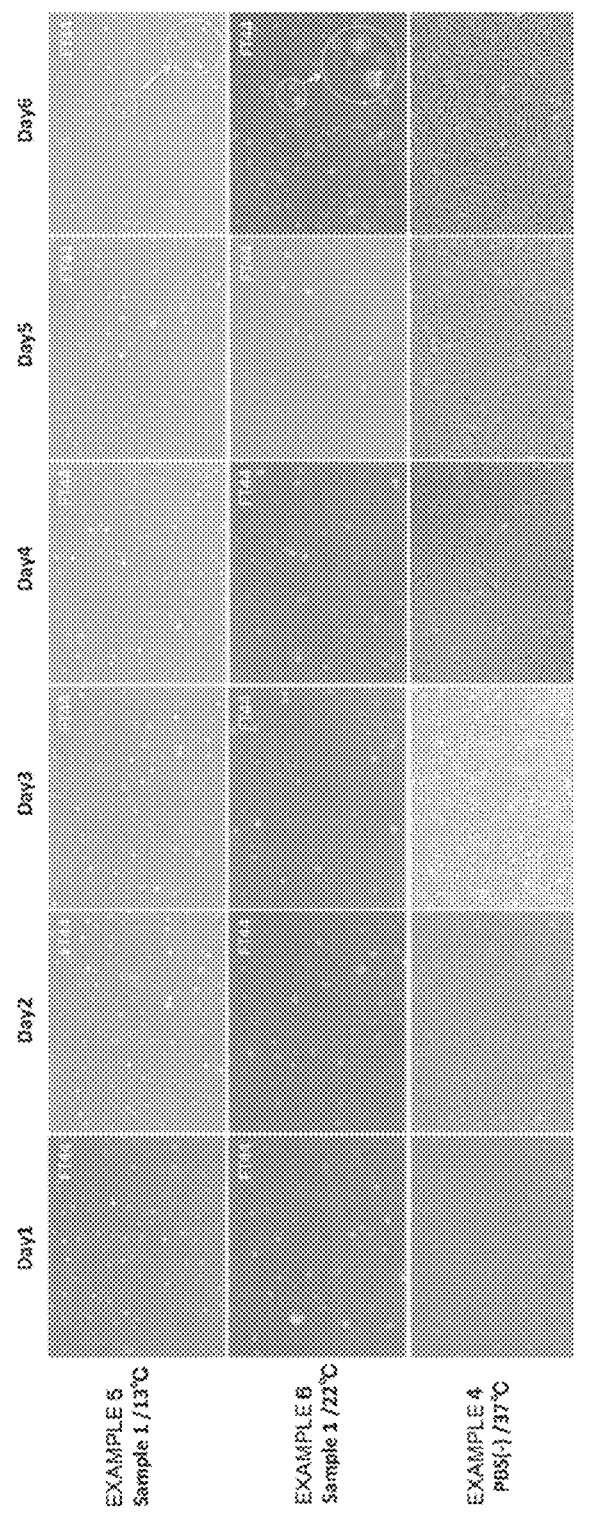

The cells in the cultures in examples 5 and 6 did not adhere to the culture container and were floating. FIG. 7 shows the results, for the cells in the example 4 to 6 test groups, of observation using a phase-contrast microscope of the cell morphology in each example on the 1st, 2nd, 3rd, 4th, 5th, and 6th days after the start of the main culture. As shown in FIG. 7, the cell morphologies in the cultures in examples 5 and 6 were clearly different from the cell morphology of the cells of example 4, where culture was carried out at a temperature condition of 37° C. without the addition of peptide to the target cell. Specifically, the cells in the cultures of examples 5 and 6 had a round cell morphology and presented a white luminance in optical microscopic observation. In other words, the cell morphology in the cultures of examples 5 and 6 was very close to a dead cell morphology. It is thought here that the excessively low culture temperatures were not only not suitable for the reprogramming (production of SIRIUS cells) of the target cell (CCD1079SK cells in this case), but were also not suitable for cell viability (proliferation).

That is, it was found that clusters with a morphology resembling that of pluripotent stem cell clusters could be rapidly (typically within 3 days) and very efficiently formed in cell culture by culturing CCD1079SK cells in the presence of sample 1. In addition, preferred temperature conditions for the induction of CCD1079SK cell reprogramming were found to be at least 25° C. and less than 37° C. (for example, at least 25° C. and not more than 35° C. and typically 30° C.).

These results show that the herein disclosed reprogramming-inducing peptide (i.e., a reprogramming-inducing agent containing this peptide) has a reprogramming-inducing activity. In other words, it is shown that the reprogramming of differentiated cells can be induced, i.e., undifferentiated cells (SIRIUS cells) can be produced, by supplying (adding) the herein disclosed reprogramming-inducing peptide to a culture (typically in the medium) where differentiated cells are being cultured and culturing the cell culture to which this peptide has been added.

Figure 2:
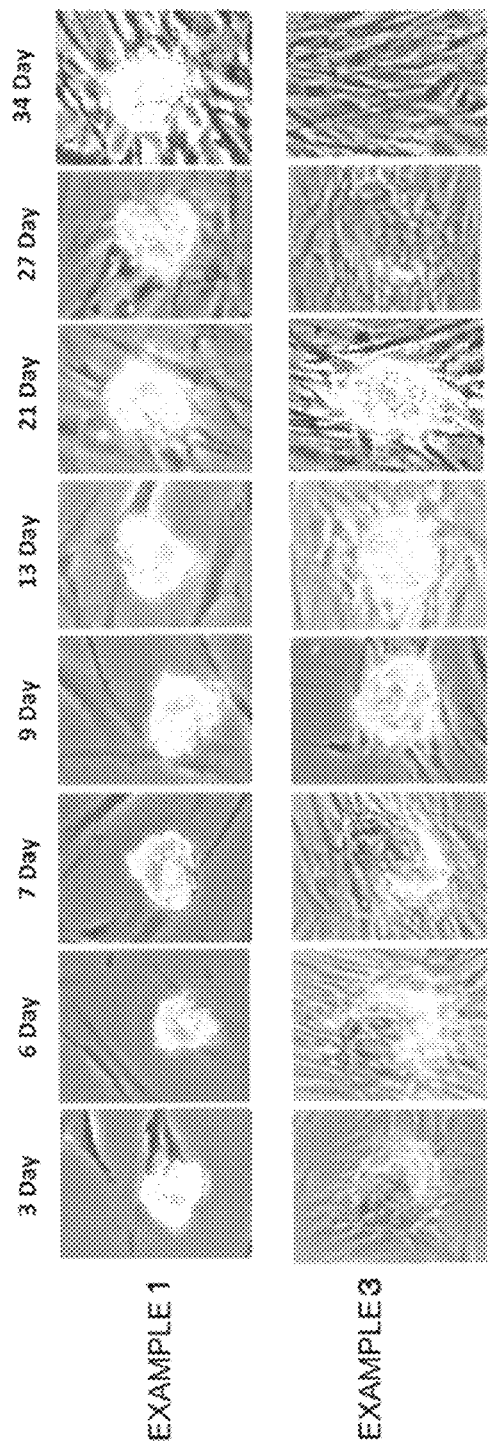
FIG. 2 contains optical micrographs (images) that show the morphology of fibroblasts that have been cultured in the presence of a reprogramming-inducing peptide (sample 1) according to a working example and in the absence of reprogramming-inducing peptide addition, wherein in each instance images are given for observation on the 3rd, 6th, 7th, 9th, 13th, 21st, 27th, and 34th days after the start of culture.
Figure 3:
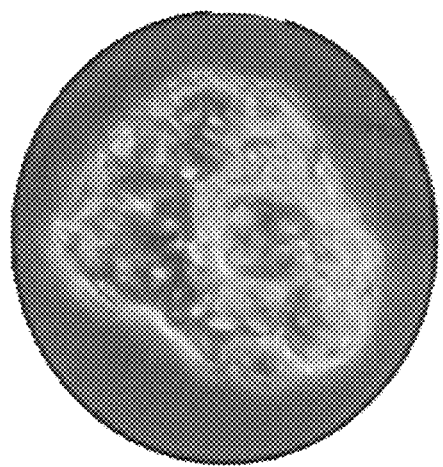
FIG. 3 is an optical micrograph (image) that shows the morphology of fibroblasts that have been cultured for 3 days in the presence of a reprogramming-inducing peptide (sample 1) according to a working example, wherein the micrograph (image) shows the morphology of cells obtained according to an embodiment of the herein disclosed method for reprogramming a differentiated cell.
Figure 4:
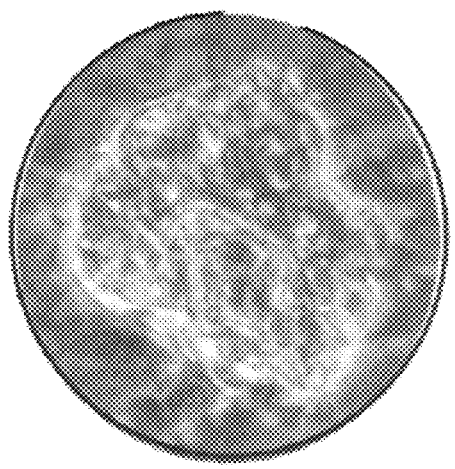
FIG. 4 is an optical micrograph (image) that shows the morphology of fibroblasts that have been cultured for 34 days in the presence of a reprogramming-inducing peptide (sample 1) according to a working example, wherein the micrograph (image) shows the morphology of cells obtained according to an embodiment of the herein disclosed method for reprogramming a differentiated cell.

As shown in FIG. 2, clusters (colonies) were found to be maintained in the culture of example 1 up to at least the 34th day after the start of the main culture under the indicated conditions. It was found that the morphology of these clusters was very similar to the morphology of clusters (colonies) of pluripotent stem cells (ES cells or iPS cells and particularly ES cells), and it was also found that the same morphology was maintained from the 3rd to at least the 34th day after the start of culture under the culture conditions in example 1. FIGS. 3 and 4 are photographs that show typical cluster morphologies as observed in example 1, and show microscopic images, observed at high amplifications, of clusters on the 3rd and 34th days after the start of culture under the culture conditions of example 1.

Figure 5:
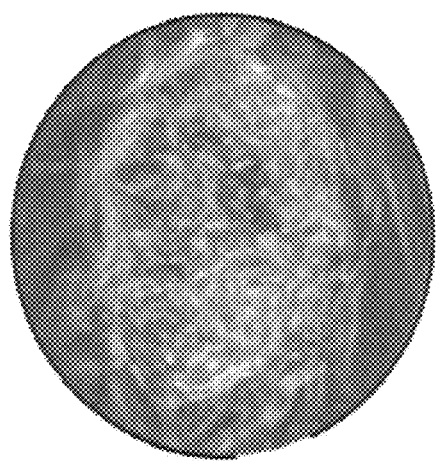
FIG. 5 is an optical micrograph (image) that shows the morphology of fibroblasts that have been cultured for 21 days without the addition of a reprogramming-inducing peptide.

In contrast to this, as shown in FIG. 2 for the rarely observed clusters in the culture in example 3, the aggregation among cells relaxed as the culture time became longer and the clusters had disappeared by around the 34th day. For the rarely observed clusters in examples 2 and 4, it was found that, as in example 3, the clusters had also disappeared by the 34th day after the start of the main culture. FIG. 5 is a photograph that shows cluster morphology as observed in examples 2 to 4 and shows a microscopic image, observed at high amplification, of a cluster on the 21st day after the start of culture under the culture conditions of example 3. Among the clusters observed in examples 2 to 4, the photograph given in FIG. 5 most resembles the cluster morphology observed in example 1.

Based on the results of these observations, it was found that, by carrying out culture on a medium that contained sample 1, the clusters formed under the culture conditions in example 1 (method for reprogramming differentiated cells according to this working example) could maintain a cluster morphology that resembled that of pluripotent stem cells and could do so on a long-term basis. This shows that, by culturing in a medium that contains the reprogramming-inducing peptide, the undifferentiated cells (SIRIUS cells) can be maintained in an undifferentiated state on a long-term basis. In other words, the herein disclosed reprogramming-inducing peptide is shown to have the ability to maintain undifferentiated cells (SIRIUS cells) in an undifferentiated state.

Working Example 3: Evaluation of the State of Undifferentiation of SIRIUS Cells

The state of undifferentiation of the SIRIUS cells (cells forming clusters) produced using the sample 1 obtained in example 1 was evaluated by cytoimmunostaining (fluorescent immunostaining) of the state of expression of undifferentiated marker genes (endogenous Oct3/4, Nanog, Sox2, TRA1-81, SSEA-3, and ALP), i.e., the state of expression of protein that is a gene product of these genes (this protein is also referred to as "undifferentiated marker protein" below). The details of the evaluation test are as follows.

The SIRIUS cells according to this working example were produced by culture under the same conditions as the culture conditions given in example 1 of Working Example 2 with the following exceptions: a cell culture chamber having 1 well per slide (culture area of 19 mm×44 mm) (also referred to as a slide chamber) was used as the culture chamber; $1.5 \times 10^5$ cells/well was used for the number of cells per well; and 1 mL was used for the amount of medium per well. The status of differentiation of the SIRIUS cells was evaluated by cytoimmunostaining as follows on the 3rd day after the start of the main culture (culture in the presence of peptide).

Fixing, a permeabilization treatment, and a blocking treatment were first carried out on the cells in each test group. Specifically, the medium was removed from the culture chamber (slide chamber) in each test group once the culture for 3 days in the presence of peptide had been completed and the cells in each slide chamber were washed with cold PBS. PBS containing 4 volume % paraformaldehyde (4% paraformaldehyde solution) was then added to the slide chamber and the cells were fixed by standing for 15 minutes on ice. After the prescribed time had elapsed, the 4% paraformaldehyde solution was removed and the cells in the slide chamber were washed with cold PBS.

PBS containing 0.25 volume % Triton (registered trademark) X-100 (0.25% Triton (registered trademark) X-100 solution) was then added to each slide chamber and a permeabilization treatment was carried out on the cell membrane by standing for 15 minutes on ice. After the prescribed time had elapsed, the 0.25% Triton (registered trademark)

X-100 solution was removed and the cells in the slide chamber were washed with cold PBS.

PBS containing 1% BSA (1% BSA-containing PBS) was added to each slide chamber and a blocking treatment was carried out for 1 hour at room temperature. After the prescribed time had elapsed, the 1% BSA-containing PBS was removed and the cells in the slide chamber were washed with cold PBS.

The primary antibodies (primary antibody dilution)—obtained by the dilution at the prescribed ratio (dilution ratio shown in Table 2) with 0.1% BSA/PBS of primary antibody that recognized the particular undifferentiated marker protein—were respectively added to the slide chambers and standing was carried out overnight (approximately 16 to 18 hours) at 4° C. After the prescribed time had elapsed, the primary antibody dilution was removed and washing with cold PBS was performed.

Table 2 gives the undifferentiation markers used to evaluate the status of expression in this working example, the details for the primary antibody (product name, product number, immunized animal, antibody class) used to recognize the particular undifferentiated marker protein, and the dilution ratio for the primary antibody. Of the primary antibodies given in Table 2, the anti-Oct3/4 antibody was from Santa Cruz Biotechnology, Inc. and the anti-Nanog antibody, anti-Sox2 antibody, anti-TRA1-81 antibody, anti-SSEA-3 antibody, and anti-ALP antibody were from Abcam plc.

TABLE 2

| undifferentiated marker | product name | product number (Cat. No.) | immunized animal | class | dilution ratio |
|---|---|---|---|---|---|
| Oct3/4 | Oct-3/4 (C-10) | sc-5279 | mouse | IgG | 50X |
| Nanog | Anti-Nanog antibody | ab80892 | rabbit | IgG | 100X |
| Sox2 | Anti-Sox2 antibody [57CT23.3.4] | ab75485 | mouse | IgG | 100X |
| TRA1-81 | Anti-TRA-1-81 [TRA-1-81] antibody | ab16289 | mouse | IgM | 100X |
| SSEA-3 | Anti-SSEA3 antibody [MC631] | ab16286 | rat | IgM | 200X |
| ALP | Anti-Alkaline Phosphatase antibody [4H1] | ab54778 | Mouse | IgG | 50X |

Secondary antibody (secondary antibody dilution)—obtained by the 1000× dilution with 0.1% BSA/PBS of a secondary antibody that detected the particular primary antibody—was added to the slide chamber and standing was carried out in the dark for 2 hours at room temperature. After the prescribed time had elapsed, the secondary antibody dilution was removed and washing with cold PBS was performed.

A fluorescence-labeled secondary antibody labeled with a fluorescent dye (Alexa Fluor (registered trademark) 555) was used to detect the anti-Oct3/4 antibody, while fluorescence-labeled secondary antibodies labeled with a fluorescent dye (Alexa Fluor (registered trademark) 488) were used to detect the anti-Nanog antibody, anti-Sox2 antibody, anti-TRA1-81 antibody, anti-SSEA-3 antibody, and anti-ALP antibody. The targeted undifferentiated markers and the details for the secondary antibody (product name, product number, immunized animal) used to detect the primary antibody that recognized the particular undifferentiated marker protein are given in Table 3. All of the secondary antibodies shown in Table 3 were from Life Technologies Corporation.

TABLE 3

| undifferentiated marker | production name | product number (Cat. No.) | immunized animal |
|---|---|---|---|
| Oct3/4 | Alexa Fluor (registered trademark) 555 Goat Anti-Mouse IgG Antibody | A-21422 | goat |
| Nanog | Alexa Fluor (registered trademark) 488 Goat Anti-Rabbit IgG Antibody | A-11008 | goat |
| Sox2 | Alexa Fluor (registered trademark) 488 Goat Anti-Mouse IgG Antibody | A-11001 | goat |
| TRA1-81 | Alexa Fluor (registered trademark) 488 Goat Anti-Mouse IgM Antibody | A-21042 | goat |
| SSEA-3 | Alexa Fluor (registered trademark) 488 Goat Anti-Rat IgM Antibody | A-21212 | goat |
| ALP | Alexa Fluor (registered trademark) 488 Goat Anti-Mouse IgG Antibody | A-11001 | goat |

The cells in each test group that had been subjected to this cytoimmunostaining were mounted using a cover glass and Slow Fade (Life Technologies Corporation, Cat. No. S36936), which is a DAPI (4',6-diamidino-2-phenylindole)-containing mountant.

Fluorescence observation using a confocal laser microscope and differential interference contrast (DIC) observation were performed on each sample (each slide) on which the cytoimmunostaining as described above had been carried out. The results are given in FIG. 6. These images are micrographs (images) probing the morphology of the CCD1079SK cells (for example, the state of aggregation) and the status of expression of the undifferentiated marker genes (i.e., presence of protein that is a gene product of the gene) after culture for 3 days in the presence of sample 1 and under a temperature condition of 30° C. Specifically, the photographs (images) shown in the left column (DIC column) are micrographs in which the cell morphology is probed by DIC observation (DIC images). The photographs (images) shown in the central column (Undifferentiated Marker column) are fluorescence micrographs (FL images) that examine the results of probing the status of the expression of the undifferentiated marker genes by observation by fluorescence observation of the undifferentiated marker protein labeled by the aforementioned immunostaining. The photographs (images) shown in the right column (Merge column) are images obtained by stacking (merging) a DAPI nuclear-stained image with the FL image given in the central column that examined the results of probing the status of expression of the particular undifferentiated marker gene.

Figure 6:
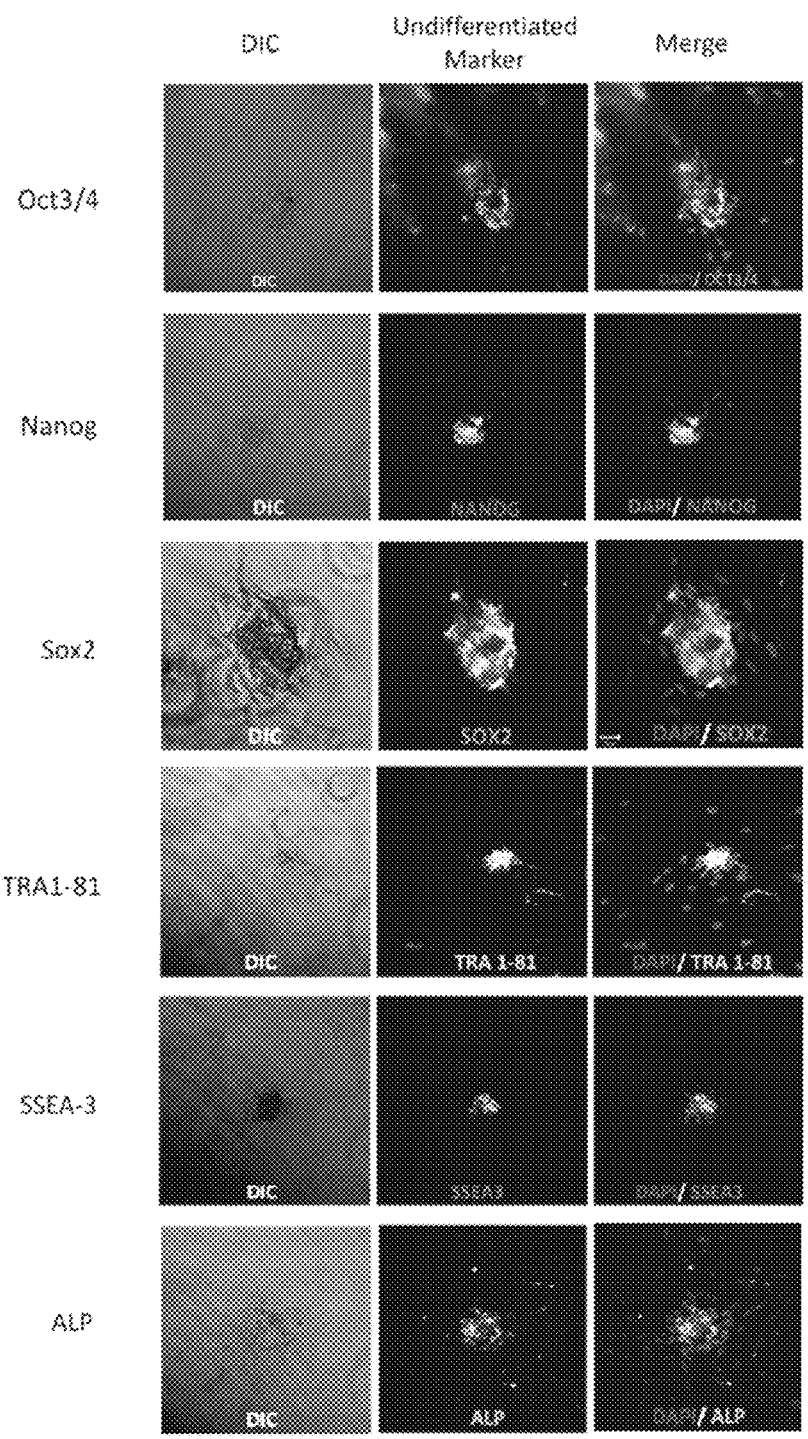
FIG. 6 contains micrographs (images) that show the morphology of cells obtained according to a working example and the status of the expression (typically the presence of the particular protein that is the gene product of the particular gene) of undifferentiated marker genes (Oct3/4, Nanog, Sox2, TRA1-81, SSEA-3, ALP), wherein the photographs (images) shown in the left column (DIC column) are micrographs in which the morphology of the cell is probed by DIC observation (DIC images), the photographs (images) shown in the central column (Undifferentiated Marker column) are fluorescence micrographs (FL images) in which the status of the expression of the undifferentiated marker genes is probed by fluorescence observation, and the photographs (images) shown in the right column (Merge column) are images obtained by stacking (merging) the FL image in the central column with a DAPI nuclear-stained image.

As shown in FIG. 6, the results of this evaluation test showed that Oct3/4, Nanog, Sox2, TRA1-81, SSEA-3, and ALP, which are undifferentiated marker genes, were strongly expressed by cells constituting the clusters formed by culture in the presence of sample 1. This demonstrates that the cells constituting these clusters are cells in an undifferentiated state (SIRIUS cells). That is, the undifferentiated cells (SIRIUS cells) produced by the herein disclosed method for producing undifferentiated cells were shown to strongly express the undifferentiated marker genes Oct3/4, Nanog, Sox2, TRA1-81, SSEA-3, and ALP.

These results show that the herein disclosed reprogramming-inducing peptide (i.e., the reprogramming-inducing agent containing this peptide) has a reprogramming-inducing activity. In other words, it is demonstrated that the reprogramming of a differentiated cell can be induced, i.e., an undifferentiated cell (SIRIUS cell) can be produced, by supplying (adding) the herein disclosed reprogramming-inducing peptide to a culture (typically in the culture medium) on which the differentiated cell is cultured and culturing the cell culture to which the peptide has been supplied.

Working Example 4: Preparation of a Granular Formulation 50 mg of sample 1 was mixed with 50 mg crystalline cellulose and 400 mg lactose, followed by the addition of 1 mL of an ethanol/water mixed solution and kneading. The kneadate was granulated by a common method to obtain a granular formulation (granular composition) in which the herein disclosed reprogramming-inducing peptide was the principal component.

INDUSTRIAL APPLICABILITY

As has been described in the preceding, the herein disclosed reprogramming-inducing peptide (and reprogramming-inducing agent containing this peptide) has a reprogramming-inducing activity that induces the reprogramming of a differentiated cell. Due to this, it can be favorably used for the purpose of reprogramming a differentiated cell or for the purpose of producing an undifferentiated cell. In addition, an undifferentiated cell can be produced by reprogramming a differentiated cell using the herein disclosed method for producing an undifferentiated cell. The undifferentiated cell produced by this method can be advantageously used as a cell resource for application in regenerative medicine.

(Sequence Listing Free Text)

SEQ ID NOs: 1 to 6 Synthetic peptide

The invention claimed is:

1. A method for producing an undifferentiated cell by reprogramming at least one type of differentiated cell, the method comprising:
preparing a cell culture that contains a target cell;
supplying an artificially synthesized peptide that induces reprogramming of at least one type of differentiated cell to the cell culture;
wherein the peptide comprises a reprogramming-inducing peptide sequence formed of the following amino acid sequence:

CKSKSRRSC (SEQ ID NO: 1)

or a modified amino acid sequence formed by conservative substitution of one, two or three amino acid residues in the amino acid sequence and that induces reprogramming in at least one type of differentiated cell; and
culturing the cell culture to which the peptide has been supplied and thereby inducing reprogramming of the target cell.

2. The production method according to claim 1, wherein the total number of amino acid residues constituting the peptide chain is not more than 30.

3. The production method according to claim 1, wherein the peptide is supplied to the cell culture with at least one pharmaceutically acceptable carrier.

4. The production method according to claim 1, wherein the differentiated cell is a human fibroblast.

5. The production method according to claim 4, wherein the differentiated cell is a human fibroblast of epidermal tissue origin.

6. The production method according to claim 1, wherein the peptide is artificially produced by chemical synthesis.

7. The production method according to claim 1, wherein the peptide is artificially produced by biosynthesis.

8. The production method according to claim 1, wherein the differentiated cell is a fibroblast of non-human mammal origin.

9. The production method according to claim 1, wherein the undifferentiated cell expresses one or more endogenous genes selected from the group of Oct3/4, Nanog, Sox2, TRA1-81, SSEA-3, and alkaline phosphatase.

* * * * *